US009005284B2

(12) United States Patent
Ressemann

(10) Patent No.: US 9,005,284 B2
(45) Date of Patent: Apr. 14, 2015

(54) METHOD AND APPARATUS FOR TREATING DILATING THE ETHMOID INFUNDIBULUM

(71) Applicant: Entellus Medical, Inc., Plymouth, MN (US)

(72) Inventor: Thomas V. Ressemann, St. Cloud, MN (US)

(73) Assignee: Entellus Medical, Inc., Plymouth, MN (US)

( * ) Notice: Subject to any disclaimer, the term of this patent is extended or adjusted under 35 U.S.C. 154(b) by 63 days.

(21) Appl. No.: 13/649,933

(22) Filed: Oct. 11, 2012

(65) Prior Publication Data
US 2013/0041463 A1 Feb. 14, 2013

Related U.S. Application Data

(63) Continuation of application No. PCT/US2011/032701, filed on Apr. 15, 2011.

(60) Provisional application No. 61/324,491, filed on Apr. 15, 2010.

(51) Int. Cl.
A61F 2/18 (2006.01)
A61M 29/00 (2006.01)
A61M 29/02 (2006.01)
A61B 17/02 (2006.01)
A61B 17/00 (2006.01)
A61M 25/10 (2013.01)

(52) U.S. Cl.
CPC ............ A61M 29/02 (2013.01); A61B 17/0218 (2013.01); A61B 2017/00557 (2013.01); A61M 25/10 (2013.01); A61M 2210/0618 (2013.01)

(58) Field of Classification Search
CPC .................................. A61F 2/18; A61M 29/00
USPC ............................ 623/10; 604/181–196, 506; 606/190–199
See application file for complete search history.

(56) References Cited

U.S. PATENT DOCUMENTS 2,525,183 A 10/1950 Robison
3,800,788 A 4/1974 White
(Continued)

FOREIGN PATENT DOCUMENTS

AT 384945 B 1/1988
DE 3536516 A1 4/1987
(Continued)

OTHER PUBLICATIONS

PCT International Search Report for PCT/US2011/032701, Applicant: Entellus Medical, Inc., Form PCT/ISA/210 and 220, dated Jul. 7, 2011 (4pages).

(Continued)

Primary Examiner — Yashita Sharma
(74) Attorney, Agent, or Firm — Vista IP Law Group LLP

(57) ABSTRACT

A method of dilating an infundibular space within the human head includes directing at least a distal portion of an elongate member of a medical device into a nasal cavity of the human head, the distal portion including a piercing tip and an expandable portion. The piercing tip is directed through tissue of an uncinate process or tissue near an uncinate process and into an ethmoid infundibulum and the expandable portion of the distal end is expanded within the ethmoid infundibulum.

13 Claims, 5 Drawing Sheets

(56) References Cited

U.S. PATENT DOCUMENTS

| | | |
|---|---|---|
| 4,737,141 A | 4/1988 | Spits |
| 5,021,043 A | 6/1991 | Becker et al. |
| 5,024,658 A | 6/1991 | Kozlov et al. |
| 5,112,299 A | 5/1992 | Pascaloff |
| 5,169,386 A | 12/1992 | Becker et al. |
| 5,490,860 A | 2/1996 | Middle et al. |
| 5,632,762 A | 5/1997 | Myler |
| 5,645,528 A | 7/1997 | Thome |
| 5,795,325 A | 8/1998 | Valley et al. |
| 5,964,223 A | 10/1999 | Baran |
| 5,964,767 A | 10/1999 | Tapia et al. |
| 6,083,188 A | 7/2000 | Becker |
| 6,090,132 A | 7/2000 | Fox |
| 6,113,567 A | 9/2000 | Becker |
| 6,238,364 B1 | 5/2001 | Becker |
| 6,355,050 B1 * | 3/2002 | Andreas et al. ............... 606/144 |
| 6,391,016 B2 | 5/2002 | Bays |
| 6,491,940 B1 | 12/2002 | Levin |
| 6,543,452 B1 | 4/2003 | Lavigne |
| D501,677 S | 2/2005 | Becker |
| 6,851,424 B2 | 2/2005 | Scopton |
| 7,070,574 B2 | 7/2006 | Jackson et al. |
| 7,520,876 B2 | 4/2009 | Ressemann et al. |
| 7,678,099 B2 | 3/2010 | Ressemann et al. |
| 7,842,062 B2 | 11/2010 | Keith et al. |
| 7,879,061 B2 | 2/2011 | Keith et al. |
| 7,918,871 B2 | 4/2011 | Truitt et al. |
| 8,241,266 B2 | 8/2012 | Keith et al. |
| 8,277,478 B2 | 10/2012 | Drontle et al. |
| 8,282,667 B2 | 10/2012 | Drontle et al. |
| 8,348,969 B2 | 1/2013 | Keith et al. |
| 8,568,439 B2 | 10/2013 | Keith et al. |
| 8,585,728 B2 | 11/2013 | Keith et al. |
| 8,585,729 B2 | 11/2013 | Keith et al. |
| 8,623,043 B1 | 1/2014 | Keith et al. |
| 8,657,846 B2 | 2/2014 | Keith et al. |
| 8,801,670 B2 | 8/2014 | Drontle et al. |
| 2002/0138121 A1 | 9/2002 | Fox |
| 2004/0064083 A1 | 4/2004 | Becker |
| 2004/0064150 A1 | 4/2004 | Becker |
| 2004/0236313 A1 | 11/2004 | Klein |
| 2005/0203489 A1 | 9/2005 | Saadat et al. |
| 2005/0240147 A1 | 10/2005 | Makower et al. |
| 2005/0245906 A1 | 11/2005 | Makower et al. |
| 2006/0004286 A1 | 1/2006 | Chang et al. |
| 2006/0004323 A1 | 1/2006 | Chang et al. |
| 2006/0063973 A1 | 3/2006 | Makower et al. |
| 2006/0095066 A1 | 5/2006 | Chang et al. |
| 2006/0100687 A1 | 5/2006 | Fahey et al. |
| 2006/0106361 A1 | 5/2006 | Muni et al. |
| 2006/0149310 A1 | 7/2006 | Becker |
| 2006/0210605 A1 | 9/2006 | Chang et al. |
| 2007/0005094 A1 | 1/2007 | Eaton et al. |
| 2007/0073269 A1 | 3/2007 | Becker |
| 2007/0250105 A1 | 10/2007 | Ressemann et al. |
| 2008/0015472 A1 | 1/2008 | Ressemann et al. |
| 2008/0015497 A1 | 1/2008 | Keith et al. |
| 2008/0015544 A1 | 1/2008 | Keith et al. |
| 2008/0015626 A1 | 1/2008 | Keith et al. |
| 2008/0033353 A1 | 2/2008 | Truitt et al. |
| 2008/0097239 A1 | 4/2008 | Chang et al. |
| 2008/0172033 A1 | 7/2008 | Keith et al. |
| 2008/0249500 A1 | 10/2008 | Keith et al. |
| 2009/0216196 A1 | 8/2009 | Dontle et al. |
| 2009/0221988 A1 | 9/2009 | Ressemann et al. |
| 2010/0076269 A1 | 3/2010 | Makower et al. |
| 2010/0211007 A1 | 8/2010 | Lesch et al. |
| 2010/0274222 A1 | 10/2010 | Setliff, III et al. |
| 2011/0071349 A1 | 3/2011 | Drontle et al. |
| 2011/0224652 A1 | 9/2011 | Drontle et al. |
| 2012/0010646 A1 | 1/2012 | Keith et al. |
| 2012/0071727 A1 | 3/2012 | Hanson et al. |
| 2012/0283625 A1 | 11/2012 | Keith et al. |
| 2013/0030458 A1 | 1/2013 | Drontle et al. |
| 2013/0030459 A1 | 1/2013 | Drontle et al. |
| 2013/0041463 A1 | 2/2013 | Ressemann |
| 2013/0072958 A1 | 3/2013 | Ressemann et al. |
| 2013/0123833 A1 | 5/2013 | Lesch et al. |

FOREIGN PATENT DOCUMENTS

| | | |
|---|---|---|
| DE | 3736604 A1 | 11/1989 |
| EP | 0129637 A1 | 1/1985 |
| EP | 0624349 B1 | 1/1997 |
| EP | 1598015 | 11/2005 |
| FR | 2612402 A1 | 9/1988 |
| WO | WO 91/17787 A1 | 11/1991 |
| WO | WO 2005086945 | 9/2005 |

OTHER PUBLICATIONS

PCT Written Opinion of the International Search Authority for PCT/US2011/032701, Applicant: Entellus Medical, Inc., Form PCT/ISA/237, dated Jul. 7, 2011 (6pages).

Entellus Medical, 510(k) Premarket Notification cover letter and Attachment B: Predicate Device Labeling, dated Aug. 15, 2007.

Folweiler, David S., Nasal Specific Technique as Part of a Chiropractic Approach to Chronic Sinusitis and Sinus Headaches, Journal of Manipulative and Physiological Therapeutics, vol. 18, No. 1, (Jan. 1995).

Lavigne, F., et al., "Selective Irrigation of the Sinuses in the Management of Chronic Rhinosinusitis Refractory to Medical Therapy: A Promising Start," The Journal of Otolaryngology, vol. 33, Nov. 1, 2004, pp. 10-16.

PCT International Search Report for PCT/US08/59236, Applicant: Entellus Medical, Inc., Form PCT/ISA/210 and 220, dated Jun. 4, 2009 (3 pages).

PCT Written Opinion of the International Search Authority for PCT/US08/59236, Applicant: Entellus Medical, Inc., Form PCT/ISA/237, dated Jun. 4, 2009 (4 pages).

PCT International Preliminary Report on Patentability (Chapter I of the Patent Cooperation Treaty) for PCT/US2008/059236, Applicant: Entellus Medical, Inc., Form PCT/IB/326 and 373, facsimile date Feb. 23, 2010 (8 pages).

PCT International Search Report for PCT/US07/66187, Applicant: Entellus Medical, Inc., Form PCT/ISA/210 and 220, dated Apr. 17, 2008 (5 pages).

PCT Written Opinion of the International Search Authority for PCT/US07/66187, Applicant: Entellus Medical, Inc., Form PCT/ISA/237, dated Apr. 17, 2008 (5 pages).

International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2008 (4 pages).

PCT International Search Report for PCT/US07/088834, Applicant: Entellus Medical, Inc., Form PCT/ISA/210 and 220, dated May 20, 2008 (4 pages).

PCT Written Opinion of the International Search Authority for PCT/US07/088834, Applicant: Entellus Medical, Inc., Form PCT/ISA/237, dated May 20, 2008 (10 pages).

International Preliminary Report on Patentability (Chapter I of the Patent Cooperation Treaty) of the International Bureau for PCT/US2007/088834, Applicant: Entellus Medical, Inc., Form PCT/IB/326, dated Jul. 30, 2009 (9 pages).

PCT International Preliminary Report on Patentability (Chapter I of the Patent Cooperation Treaty) for PCT/US2011/032701, Applicant: Entellus Medical, Inc., Form PCT/IB/326 and 373, dated Oct. 26, 2012 (6pages).

Peterson, R., Sinus Puncture Therapy; Canine Fossa Puncture Method "How I Do It" Head and Neck, The Laryngoscope 91: Dec. 1981 pp. 2126-2128.

T.G.A. Ijaduola, Use of a Foley Catheter for Short-Tem Drainage of Frontal Sinus Surgery, Journ. of Laryngology and Otology, Apr. 1989, vol. 103, pp. 375-378.

Gatot, A. et al., Early Treatment of Oribital Floor Fractures with Catheter Balloon in Children, Intl. J. of Ped. Otorhinolaryngology, 21 (1991) 97-101.

(56) References Cited

OTHER PUBLICATIONS

Tarasov, D.I. et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).
Robinson, J. M., Pressure Treatment of Maxillary Sinusitis, J.A.M.A., May 31, 1952, pp. 436-440.
Robinson, J. M., Pressure Treatment of Purulent Maxillary Sinusitis, Texas State Journal of Medicine, May 1952, pp. 281-288.
Entellus Medical, 510(k) Letter (Amendment 1) and Attachments D & E, dated Mar. 13, 2008.
Petersen, R. J., Canine Fossa Puncture, The Laryngoscope Office, Oct. 5, 1972, pp. 369-371.
Elidan, J., MD., Irrigation of the Maxillary Sinus by Canine Fossa Puncture Experience with 202 Patients, Ann Otol Rhinol Laryngol, 92:1983, pp. 528-529.
Gottman, D., et al., "Balloon Dilatation of Recurrent Ostia Occlusion of the Frontal Sinus", ECR Mar. 3, 2001, 2:-3:30 PM, Vienna Austria (1 page).
Gottman et al., "Balloon Dilation of Recurrent Ostial Occlusion of the Frontal Sinus", Gottmann et al. Abstract (B-0453) Mar. 2001, 22 pages.
Yanagisawa, E. et al., Trans-Canine-Fossa Maxillary Sinoscopy for Biopsy Via the Stammberger Technique, ENT. Rhinoscopic Clinic, Aug. 2001 Rhino, pp. 1-3.
Yanagisawa, E. et al., Powered Endoscopic Inferior Meatal Antrostomy Under Canine Fossa Telescopic Guidance, ENT-Ear, Nose & Throat Journal, Sep. 2001, pp. 618-620.
Sathananthar, S. et al., Canine Fossa Puncture and Clearance of the Maxillary Sinus for the Severely Diseased Maxillary Sinus, The Laryngoscope 115: Jun. 2005, pp. 1026-1029.
Robinson, S. et al., Patterns of Innervation of the Anterior Maxilla: A Cadaver Study with Relevance to Canine Fossa Puncture of the Maxillary Sinus, Laryngoscope 115: Oct. 2005, pp. 1785-1788.
Bolger, W.E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, OceanSide Publications, Inc., May-Jun. 2006, vol. 20, No. 3, pp. 290-294.
Friedman, M., M.D. et al., Functional Endoscopic Dilatation of the Sinuses (FEDS): Patient Selection and Surgical Technique, Operative Technologies in Otolaryngology, vol. 17, No. 2, Jun. 2006, pp. 126-134.
Jones, N., Commentary on "Safety and Feasibility of Balloon Catheter Dilation of Paranasal Sinus Ostia: A Preliminary Investigation", Annals of Otology, Rhinology & Laryngology 115(4), pp. 300-301 (2006).
Bolger, W.E., Commentary Misconceptions Regarding Balloon Catheter Dilation of Paranasal Sinus Ostia, Annals of Otology, Rhinology & Laryngology 115(10): 791-792 (2006).
Lanza, D.C., et al., Commentary Balloon Sinuplasty: Not Ready for Prime Time, Annals of Otology, Rhinology & Laryngology 115(10): 789-790 (2006).
Brown, C.L., et al., "Safety and Feasibility of Balloon Catheter Dilation of Paranasal Sinus Ostia: A Preliminary Investigation", Annals of Otology, Rhinology & Laryngology 115(4):293-299 (2006).
Iro, H. et al., A new device for frontal sinus endoscopy: First Clinical Report, Department of Otorhinolaryngology, University of Eralngen-Nuremberg, Germany. Otorhinolaryngology, Head and Neck Surgery vol. 125 No. 6, Dec. 2001, pp. 613-616 (4 pages).
Goettmann, D. et al., Treatment of a Recurrent Choanal Atresia by Balloon Dilatation, Cardiovasc Intervent Raiol (2000) 23:480-481.
Hashim, AA et al., Balloon Compression of the Intramaxillary Sinus for Intractable Post-Traumatic Bleeding From the Maxillary Artery, J. Plast Reconst Hang Sug 33:321 (1999).
Matsune, S. et al., Application of YAMIK sinus catheter for patients with paranasal sinusitis with and without nasal allergy, Auris Nasus Larynx 27 (2000) 343-347.
Michel, O., Transnasale Chrirugie der Orbita, HNO (2000). 48:4-17, Springer-Verlag 2000 (in German language: please refer to the attached non-English reference Statement Certification for clarification).

* cited by examiner

METHOD AND APPARATUS FOR TREATING DILATING THE ETHMOID INFUNDIBULUM

RELATED APPLICATIONS

This Application claims priority to PCT Patent Application No. PCT/US2011/032701 filed on Apr. 15, 2011 which itself claims priority to U.S. Provisional Patent Application No. 61/324,491 filed on Apr. 15, 2010. The above-noted Applications are incorporated by reference as if set forth fully herein. Priority is claimed pursuant to 35 U.S.C. §§119, 120 and any other applicable statute.

BACKGROUND

Various methods and devices for the treatment of sinusitis have been developed over the last few decades. Some of those methods involve dilating a sinus ostia with inflatable devices (e.g., balloon catheters) that are inserted trans-nasally or via a trans-canine fossa approach.

A need exists for new and improved methods and devices for treating sinusitis.

SUMMARY OF THE INVENTION

This invention is directed towards methods and devices for treating sinusitis by dilating the ethmoid infundibulum.

In some embodiments, the invention includes methods of dilating an infundibular space that include directing at least a distal portion of an elongate member of a medical device into a nasal cavity of the human head, the distal portion including a piercing tip and an expandable portion; directing the piercing tip through tissue of an uncinate process or through tissue near the uncinate process and into an ethmoid infundibulum; and expanding the expandable portion of the distal end within the ethmoid infundibulum.

DETAILED DESCRIPTION

The ethmoid infundibulum is a curved channel or space within the sinonasal anatomy that is bounded by the lateral surface of the uncinate process anteriomedially, the ethmoid bulla posterolaterally, and the lamina papyracea anterolaterally. It has been surprisingly discovered that dilating the ethmoid infundibulum can result in improved drainage of the maxillary, some or all of the ethmoid cells, and often the frontal sinuses which can, in turn, relieve or reduce the symptoms of sinusitis, without the need to dilate the maxillary sinus ostium itself. It is believed that dilating the ethmoid infundibulum causes the uncinate process to break in certain places, resulting in permanent expansion of the infundibular space and improved drainage from the sinus cavities. It is also believed that the uncinate process heals in an orientation that typically maintains the expansion of the infundibular space, thereby resulting in permanently improved drainage from the frontal and/or maxillary sinus cavities. Other mechanisms may also result in the improvement of sinus health as a result of such expansion.

In some embodiments, the invention includes methods of dilating an infundibular space within the human head. The methods include directing at least a distal portion of an elongate member of a medical device into a nasal cavity of the human head, wherein the distal portion of the elongate member includes a piercing tip and an expandable portion. The piercing tip is directed through an uncinate process and into an ethmoid infundibulum. The expandable portion of the distal end is then expanded within the ethmoid infundibulum.

Figure 1A:
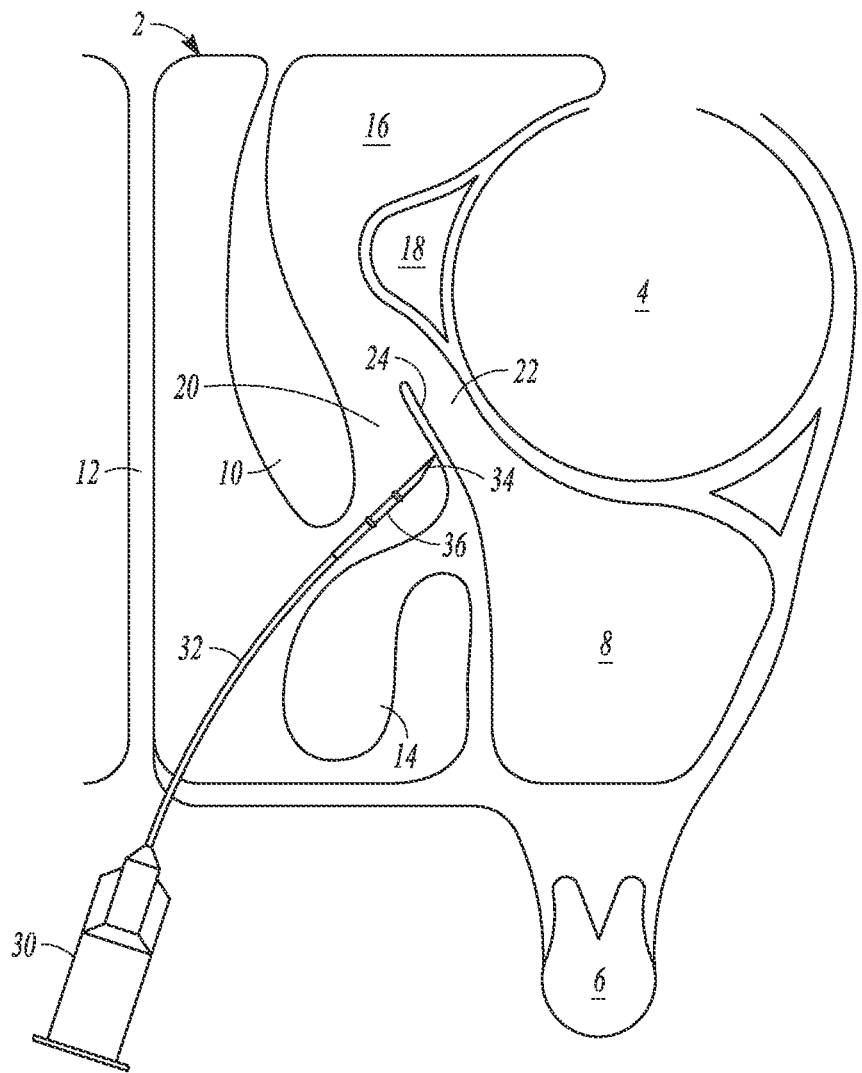
FIGS. 1A-1C illustrate a sequential representation of one embodiment of a method for treating sinusitis that include cut-away views of a human head.
Figure 1B:
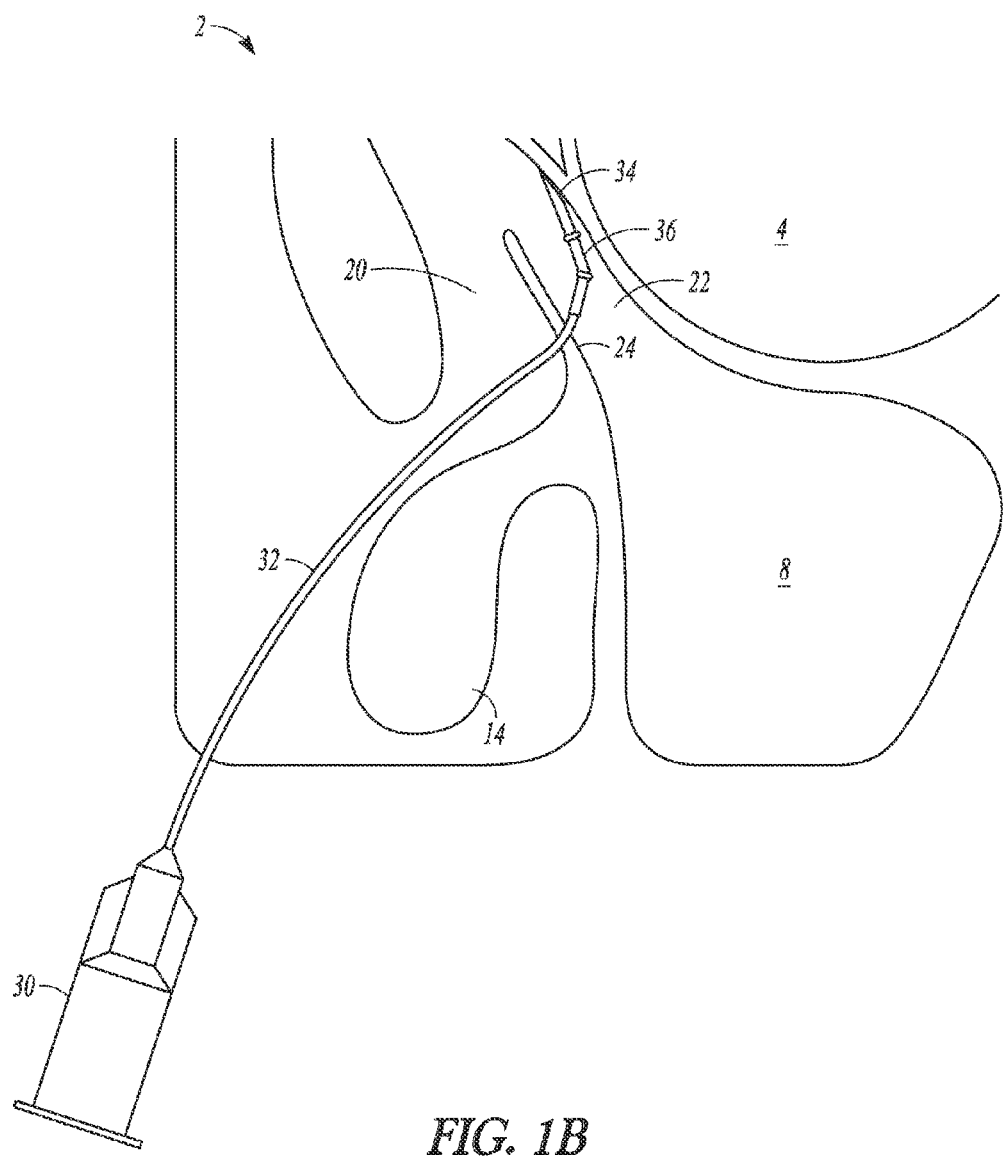
Figure 1C:
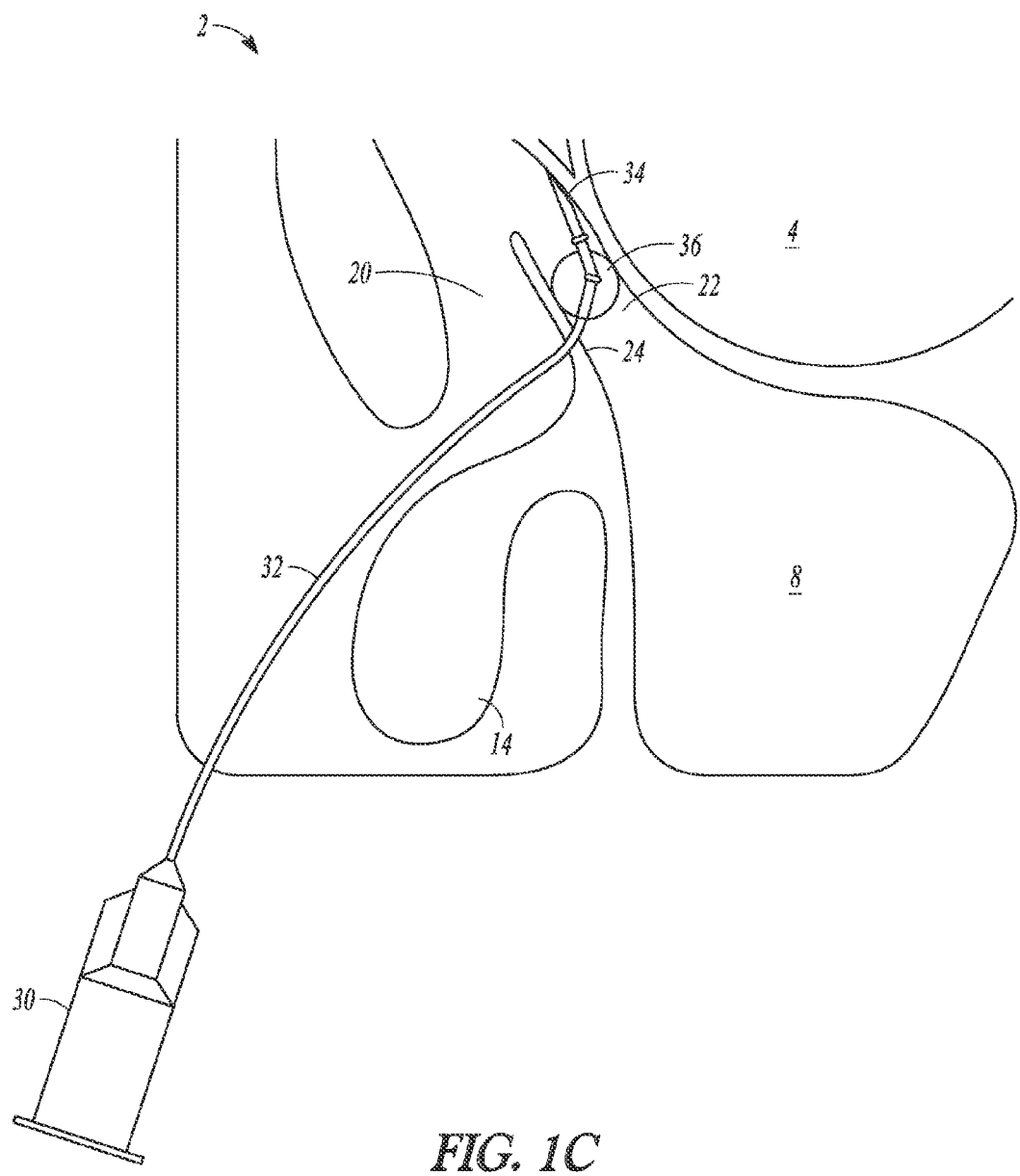

FIGS. 1A-1C illustrate a sequential representation of one of a method for treating sinusitis that includes cut-away views of human head 2 along a coronal plane that intersects left maxillary sinus cavity 8. As can be seen in FIG. 1A, head 2 includes left eye socket 4, tooth 6, left maxillary sinus cavity 8, middle turbinate 10, nasal septum 12, inferior turbinate 14, left frontal sinus cavity 16, ethmoidal bulla 18, middle meatus 20, ethmoidal infundibulum 22, and uncinate process 24. In the embodiment of the invention shown in FIGS. 1A-1C, elongate member 32 of medical device 30 is inserted through the patient's left nostril (not illustrated) and into the patient's nasal cavity.

Medical device 30 includes an elongate portion or elongate member 32 having a piercing tip 34 at the distal tip and an expandable member 36 located near and proximate to the distal tip. Medical device 30, could be, for example, a needle-tipped balloon catheter with the catheter's needle-tip serving as piercing tip 34 and the inflatable balloon (e.g., a fully compliant balloon) serving as expandable member 36. In alternative embodiments, the expandable member of the device is an expandable stent or includes deployable arms (e.g., prongs or tines that deploy from the distal portion of the elongate member).

Piercing tip 34 is directed towards a position in middle meatus 20, near or in contact with uncinate process 24 or the root of uncinate process 24, as illustrated in FIG. 1A. Piercing tip 34 is then advanced through uncinate process 24 and into ethmoidal infundibulum 22 until expandable member 36 is located within ethmoidal infundibulum 22 or on the ethmoidal infundibular side of uncinate process 24, as shown in FIG. 1B. Expandable member 36 is inflated or expanded, as shown in FIG. 1C. Expanding expandable member 36 dilates the tissue bounding ethmoidal infundibulum 22. In many cases, expanding expandable member 36 causes the bone underlying uncinate process 24 to fracture, with the bone healing relatively quickly (e.g., in a matter of days) and in a configuration that results in a permanently widened ethmoidal infundibular space.

In some embodiments of the invention, the elongate member of the medical device 30 is inserted into the human head 2 via some route other than a trans-nostril approach (e.g., via a trans-canine fossa approach).

Figure 2:
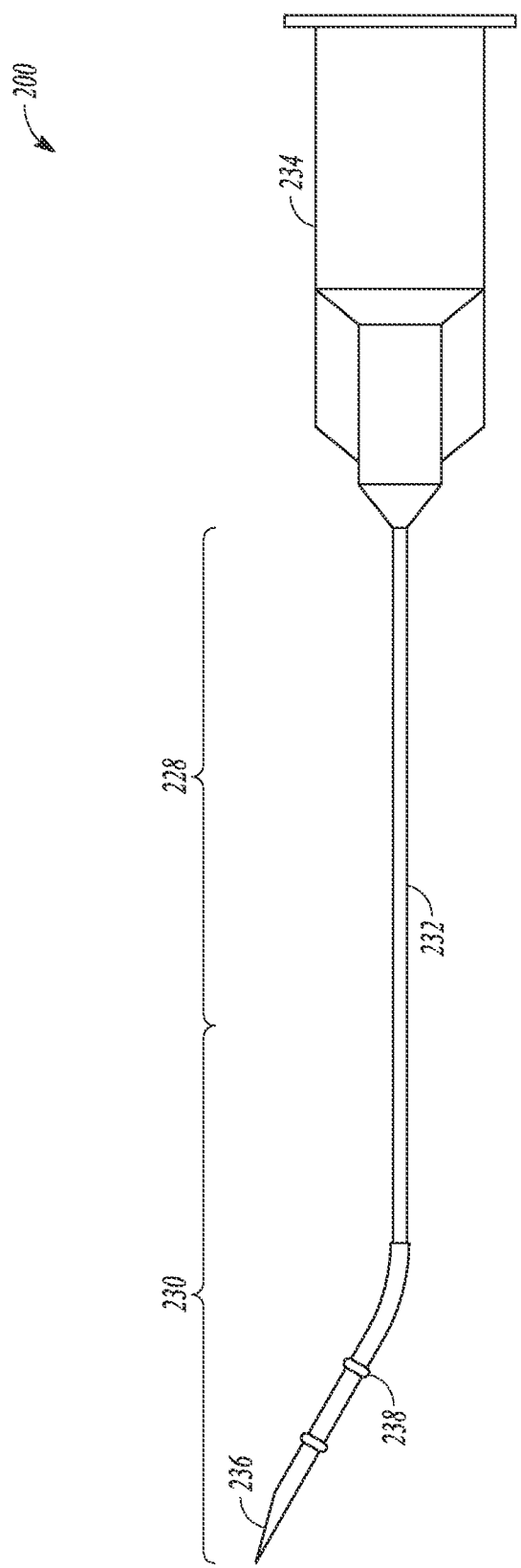
FIG. 2 illustrates a photograph of one embodiment of the invention that includes needle-tipped balloon catheter.

FIG. 2 illustrates one embodiment of the invention that includes needle-tipped balloon catheter 200. Needle-tipped balloon catheter 200 has an elongate member 232 which takes the form of a hollow hypotube having an outer diameter approximately equal to that found in standard 27-gauge hypodermic needles (~0.016 inches). In some embodiments, the elongate member has an outer diameter approximately equal to that found in standard 22-gauge hypodermic needles (~0.028 inches). On its proximal end, elongate member 232 is attached to Leur lock 234. At its distal end, elongate member 232 includes piercing tip 236. Distal end length 230 is curved compared to proximal end length 228. This curvature on distal portion of elongate member 232 allows catheter 200 to be more easily directed through and behind an uncinate process 24.

Elongate member 232 shown in FIG. 2 is relatively short. In other embodiments, the elongate member is approximately 5 to 20 cm in length while in yet other embodiments the elongate member is approximately 8 to 15 cm in length.

Also, in some embodiments, the elongate member comprises a braided tubular shaft with an expandable member (rather than a hypotube with an expandable member as shown in FIG. 2), wherein the tubular shaft has sufficient stiffness for piercing through an uncinate process and placing the expandable member within the ethmoidal infundibular space.

Figure 3:
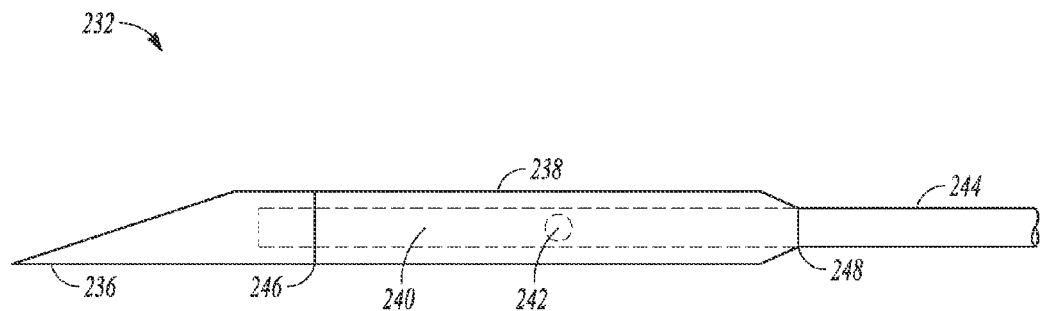
FIG. 3 illustrates a schematic diagram of a distal end of an elongate member shown in FIG. 2.

FIG. 3 illustrates a schematic representation of the distal end of elongate member 232 shown in FIG. 2. The distal end of elongate member 232 includes expandable member 238 located on hypotube 244 near or adjacent to piercing tip 236. Hypotube 244 defines inflation lumen 240 and inflation port 242. Inflation lumen 240 is in fluid communication with inflation port 242. Expandable member 238 is securely fastened to hypotube 244 at distal end 246 and proximal end 248 of expandable member 238. Between the distal and proximal ends 246, 248 expandable member 238 is situated on, but not securely fastened to, hypotube 244.

Expandable member 238 can be made from an elastomeric material that can be expanded by a fluid. Examples of suitable types of material for use as expandable member 238 include elastomeric silicone materials. Silicon materials that become relatively lubricious when wet provide an added advantage that the expandable member will be lubricated by mucous or other fluids in the human anatomy, thereby allowing the expandable member 238 to pass through tissue more easily and with less force from a practitioner of the invention. Other elastomeric or partially elastomeric materials (e.g., latex, polyurethane, and the like) could also be utilized for the expandable member. Alternatively, the expandable member could be formed of a preformed relatively inelastic membrane, which is folded and wrapped in its uninflated condition and then unfolds and expands when pressurized. Suitable materials for such a construct include polyamides (e.g., nylons), polyether block amides (e.g., PEBAX), PET, polyethylene, and the like.

During use, a fluid (e.g., water) is directed from the proximal end of elongate member 232, down the length of hypotube 244 via inflation lumen 240, out inflation port 242, and between the inner surface of expandable member 238 and outer wall of hypotube 244, thereby forcing or expanding expandable member 238 in a radial direction relative to the major axis of elongate member 232.

Figure 4:
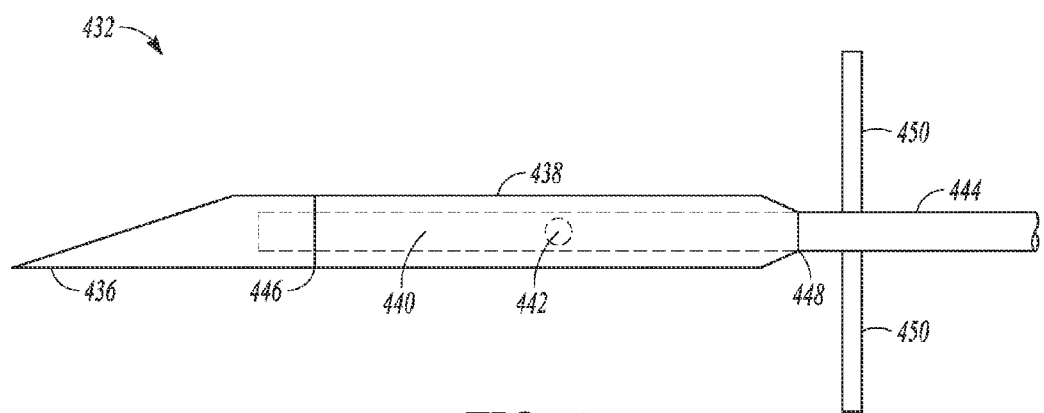
FIG. 4 illustrates a schematic diagram of a distal end of an elongate member having one form of a stopping member.

In some embodiments of the invention, the elongate member includes a stopping member near the distal tip that prevents a user from directing the piercing tip 236 further into tissue than desired. FIG. 4 illustrates such an embodiment as the distal end of elongate member 432. The distal end of elongate member 432 includes expandable member 438 located on hypotube 444 near or adjacent to piercing tip 436. Hypotube 444 defines inflation lumen 440 and inflation port 442. Inflation lumen 440 is in fluid communication with inflation port 442. Expandable member 438 is securely fastened to hypotube 444 at distal end 446 and proximal end 448 of expandable member 438. Between the distal and proximal ends 446, 448 expandable member 438 is situated on, but not securely fastened to, hypotube 444.

The distal end of elongate member 432 also includes a stopping member in the form of stopping fins 450. During use, stopping fins 450 can help the practitioner advance piercing tip 436 to the desired degree and may prevent the practitioner from advancing piercing tip 436 into tissue which he/she does not wish to pierce. For example, a practitioner can advance piercing tip 436 through an uncinate process 24 and into the ethmoidal infundibular space until stopping fins 450 abut the uncinate process 24, thereby preventing the practitioner from advancing piercing tip 436 into the maxillary sinus cavity 8 or through tissue of the eye. In some embodiments, the stopping member may be in the form of a single flange projecting from a position on hypotube 444 that is slightly proximate relative to the expandable member.

In some embodiments, the inventive methods include injecting or directing a pharmaceutical agent or medical ointment into the ethmoid infundibulum or into or onto the tissue surrounding the ethmoid infundibulum. For example, an ointment that prevents tissue surfaces form fusing during a healing process can be injected into the infundibular space or into or onto the tissue surrounding the infundibular space either through a separate injection device (e.g., a hypodermic needle) or a medical device 30 of the type described herein.

In further embodiments, the invention includes detaching the expandable member 36, 238, 428 from the elongate member 32, 232, 432. For example, the expandable member may 36, 238, 428 be left in place within the ethmoidal infundibulum in order to prop the infundibular space open while the uncinate process heals. Alternatively, or in addition, the detached expandable member 36, 238, 428 can be used to deliver drugs or other medicinally useful agents to that part of the nasal anatomy over a relatively longer period of time (e.g., days, weeks, or months). For example, the expandable member 36, 238, 428 could be a drug-eluting stent or a porous bag that expels one or more drugs over a relatively long period of time. In another example, the expandable member 36, 238, 428 may be made of a drug-containing material that slowly dissolves or is slowly absorbed by the body.

The methods and articles of this invention dilate the ethmoidal infundibular space to treat sinusitis, typically without needing further dilation of sinus ostia. While some embodiments of this invention may not require dilation of the ostia in order to treat sinusitis, other embodiments of the invention include methods where the ostia are dilated before or after the ethmoidal infundibular spaces are dilated with the devices described herein. For example, in some embodiments, this invention includes combining a method of dilating an ethmoidal infundibular space as described herein with one or more of the methods of dilating a sinus ostium as described in U.S. Pat. No. 7,520,876 issued to Ressemann, et al., the entire teachings of which are incorporated herein by reference.

The invention claimed is:

1. A method of dilating an infundibular space within the human head, the method comprising:
    directing at least a distal portion of an elongate member of a medical device into a nasal cavity of the human head, the distal portion including a piercing tip and an expandable portion;
    directing the piercing tip through tissue of an uncinate process or through tissue near the uncinate process and into an ethmoid infundibulum;
    expanding the expandable portion of the distal end within the ethmoid infundibulum; and
    detaching the expandable portion from the medical device and withdrawing the elongate member while leaving the expandable portion within the human head.

2. The method of claim 1, wherein the elongate member is advanced into the nasal cavity via a nostril.

3. The method of claim 1, wherein the expandable portion is an inflatable balloon.

4. The method of claim 3, wherein the expandable portion is a fully compliant inflatable balloon.

5. The method of claim 1, wherein the medical device is a balloon catheter and the piercing tip is a needle having an outside diameter of at least 0.016 inches or larger.

6. The method of claim 5, wherein the needle has an outside diameter of 0.028 inches.

7. The method of claim 1, wherein the expandable portion is a stent.

8. The method of claim 1, wherein the distal portion further includes a pharmaceutical agent.

9. The method of claim 1, wherein the distal portion further includes a stopping member configured to limit penetration of the piercing tip into tissue.

10. The method of claim 1, further including injecting a pharmaceutical agent into the ethmoid infundibulum.

11. The method of claim 10, wherein the agent is injected through the medical device.

12. The method of claim 1, wherein at least a portion of an outer surface of the distal portion is made from silicone.

13. The method of claim 12, wherein the expandable portion is made from silicone.

* * * * *